(12) United States Patent
Little et al.

(10) Patent No.: US 6,250,761 B1
(45) Date of Patent: Jun. 26, 2001

(54) RETINOSCOPE

(75) Inventors: Mervyn Aubrey Little, Surrey; Kelvyn Church, Reading, both of (GB)

(73) Assignee: Keeler Limited, Windsor (GB)

( * ) Notice: Subject to any disclaimer, the term of this patent is extended or adjusted under 35 U.S.C. 154(b) by 0 days.

(21) Appl. No.: 09/649,395

(22) Filed: Aug. 28, 2000

(30) Foreign Application Priority Data

Aug. 28, 1999 (GB) .................................................. 9920336

(51) Int. Cl.[7] .................................................... A61B 3/10
(52) U.S. Cl. ............................................................ 351/211
(58) Field of Search ................................... 351/200, 205, 351/211, 214, 221, 212, 218, 215, 213, 216, 219

(56) References Cited

U.S. PATENT DOCUMENTS

| | | | |
|---|---|---|---|
| 5,189,449 | * | 2/1993 | Perkins .................................. 351/211 |
| 5,528,323 | * | 6/1996 | Fujieda et al. ........................ 351/218 |
| 6,079,830 | * | 6/2000 | Kohayakawa ......................... 351/211 |

* cited by examiner

Primary Examiner—George Manuel
(74) Attorney, Agent, or Firm—Lee, Mann, Smith, McWilliams, Sweeney & Ohlson (57) ABSTRACT

A spot retinoscope is used to assess a refractive error of an eye, and has viewing means (11, 12) for viewing the eye under examination, and projection means (6, 9) for directing a beam of light from a light source (5; 82) into said eye thereby to project a spot of light onto the latter. The divergence and convergence of the beam can be altered by focusing means (6, 48) movable from a normal position in which the beam is divergent, or converges to a point (in use) behind the eye under examination, to a cross-checking position, in which the beam is convergent on a point which, in use, is sufficiently far in front of the eye under examination to enable the user to detect movement of the patch of light projected onto the retina of said eye where any refractive error in the eye has not been corrected by a lens placed between the eye and the retinoscope. The retinoscope may also be used (with a further light source) as a streak retinoscope.

13 Claims, 6 Drawing Sheets

NOTES.

1/ RADII TO BE 2-5 RINGS EDGE CONTACT UNLESS STATED OTHERWISE.

2/ SURFACE FORM TO BE WITHIN 0.5 RINGS OF A TRUE CIRCLE.

3/ SURFACE FINISH TO BE 20/10 SCRATCH & DIG.

4/ GLASS TO BE FREE FROM BUBBLES, BAD METAL AND ALL OTHER IMPERFECTIONS.

5/ CENTERING ERROR 0°5'

6/ SINGLE LAYER MAGNESIUM FLUORIDE ANTI-REFLECTIVE COATING (400-700nm) CENTRED ON 550nm

MATERIAL GLASS TYPE SF2 OR EQUIVALENT

NOTES.
1/ RADII TO BE 2-5 RINGS EDGE CONTACT UNLESS STATED OTHERWISE.
2/ SURFACE FORM TO BE WITHIN 0.5 RINGS OF A TRUE CIRCLE.
3/ SURFACE FINISH TO BE 20/10 SCRATCH & DIG
4/ GLASS TO BE FREE FROM BUBBLES, BAD METAL AND ALL OTHER IMPERFECTIONS.
5/ CENTERING ERROR 0°5'
6/ SINGLE LAYER MAGNESIUM FLUORIDE ANTI-REFLECTIVE COATING (400-700nm) CENTRED ON 550nm.

MATERIAL: GLASS TYPE BK7 OR EQUIVALENT

RETINOSCOPE

FIELD OF THE INVENTION

This invention relates to retinoscopes and more particularly to spot retinoscopes or dual mode retinoscopes which can function either as spot retinoscopes or streak retinoscopes.

BACKGROUND TO THE INVENTION

Retinoscopes are used to obtain objective indications of any refractive errors in eyes. To that end a retinoscope projects a small patch of light onto the fundus of an eye under examination. The user of the retinoscope (i.e. the person conducting the examination) then moves the device so as to move the emitted beam in a given direction, and views the direction in which the patch appears to move after having been refracted and reflected by the eye under examination. The direction of the apparent movement of the patch, relative to the actual movement of the retinoscope, enables the user to determine whether the eye under examination is long-sighted or short-sighted. The user can then quantify the refractive error of the eye under examination by interposing correction lenses of various strengths between the eye under examination and the retinoscope until the user finds a correction lens for which movement of the retinoscope causes substantially no apparent movement of the patch of light. This is referred to the "neutral point" of the eye under examination, and the power of the correction lens that achieves this is indicative of the refractive error.

A conventional spot retinoscope has a light source, such as a light bulb with a conventional helical filament, light from which passes through a focusing lens system, and is then reflected by an angled, semi-silvered or apertured mirror into the eye under examination. An annular stop is interposed between the lens system and the light source, and the shadow cast by the stop defines the boundary of the substantially circular patch of light projected into the eye under examination. The image of the patch of light projected into the eye is viewed by the user from the opposite side of the mirror.

Known spot retinoscopes also have a facility for moving the lens system so as to alter the divergence of the beam of light being directed into the eye under examination, so as to enable the user to alter the size of the projected spot. Large refractive errors cause slow movements of the reflex which are difficult to detect if the spot is large. By reducing the spot size, the movement is made easier to detect. Small refractive errors cause fast movements and are more easily detected when the spot is large.

However, even with a large spot, it can be difficult to determine whether the neutral point has in fact been reached, or whether there is a small amount of movement of the projected spot. Thus, errors in the determination of refractive error can occur if the user of the retinoscope believes the neutral point has been reached, whereas in fact movement of the retinoscope does cause a small undetected amount of movement of the projected spot.

SUMMARY OF THE INVENTION

According to the invention, there is provided a spot retinoscope for use in assessing the of refractive error of an eye, the retinoscope having viewing means for viewing the eye under examination, receiving means for receiving a source of light, projection means for directing a beam of light into an eye under examination thereby to project a spot of light into said eye, and focusing means for altering the divergence and convergence of said beam, the focusing means being movable from a normal position in which the beam is divergent, or converges to a point, in use, behind the eye under examination, to a cross-checking position, in which the beam is convergent on a point which, in use, is sufficiently far in front of the eye under examination to enable the user to detect movement of the patch of light projected onto the retina under examination where any refractive error in said eye has not been corrected by a lens placed between the eye and the retinoscope.

Even if movement of the retinoscope causes only a very small amount of perceived movement of the projected spot in the eye under examination when the focusing means is in its normal position, it has been found that the same movement of the retinoscope will produce movement of the projected spot in the opposite direction when the focusing means is in its cross-check position. Thus, when the user has found what is believed to be the "neutral point" for a patient, using the focusing means is in its normal position, the user can check to determine whether the neutral point has in fact been reached by moving the focusing means into its cross-check position. If the neutral point has been reached, movement of the retinoscope will still not cause perceived movement of the projected spot, whereas there will be a detectable movement of the spot if the neutral point has not been reached.

Thus, the invention enables the user to confirm that the neutral point has been reached.

In the past, a similar type of cross-checking has been performed using certain design of streak retinoscopes. However, as far as the Applicants are aware, those streak retinoscopes were not specifically designed to have a cross-checking feature, and the focusing systems of known spot retinoscopes do not have a position corresponding to the cross-check position of the focusing means of the present invention.

Preferably, when in its cross-check position, the focusing means is so arranged that, in use, it causes the beam of light emitted by the retinoscope to converge on a point not more than approximately 300 mm from the retinoscope.

It has been found that, with a retinoscope at normal viewing distances from the eye, any movement of the projected spot when the focusing means is in its cross-check position is greatly reduced if the point of convergence is any closer to the eye than 300 mm.

It will be appreciated that the invention is not restricted to retinoscopes which are supplied with their own light sources, since the light source for a retinoscope would normally be replaceable. Thus, the invention includes within its scope a retinoscope which does not have an integral light source, but is intended for use with a separately supplied source.

Conveniently, however, the retinoscope does include a light source for emitting the light for said beam.

Preferably, the light source is interchangeable with a further light source, the further light source being arranged to emit light over an elongated substantially linear area to cause the retinoscope to project a streak of light into the eye under examination, the retinoscope including rotation means for rotating the streak to enable to retinoscope to be used as a streak retinoscope.

Preferably, the further light source has a linear light-emitting element, for example a filament, the projected image of which constitutes said streak.

The retinoscope may to advantage include a stop, preferably an annular stop, situated in the path of light from the light source and arranged to cast a shadow that bounds the beam of light projected from the retinoscope so as to cause a spot of light to be projected into the eye under examination, the light source being such as to provide substantially uniform illumination of the spot.

To that end, the light source may, for example, comprise a bulb having a helical filament.

Where the retinoscope can be used as a spot or as a streak retinoscope, the range of movement of the focusing means is preferably such as to enable an image of either the inner periphery of the stop or, where the further light source is used, the linear element to be projected into the eye under examination.

To that end, the focusing means may to advantage comprise lens means which is slidably mounted in the retinoscope and is movable towards or away from the stop and light source over a distance of at least 14 mm.

It has been found, with this range of movement, the lens means can not only enable the retinoscope to be used as a spot retinoscope or streak retinoscope (depending on the nature of the light source used), but can also allow the retinoscope to be used to provide the above described cross-check in either its spot or its streak modes of operation.

Preferably, the focusing means is in its cross-check position when the lens means is furthest from the stop and light source.

Preferably, the rotation means and focusing means are connected to an external control member, for operating the rotation means and adjusting the position of the focusing means, by a magnetic linkage.

Preferably, the control member comprises a sleeve which is slidably and rotatably mounted on the exterior of the retinoscope.

BRIEF DESCRIPTION OF THE DRAWINGS

The invention will now be described, by way of example only, with reference to the accompanying drawings in which.

DETAILED DESCRIPTION

Figure 1:
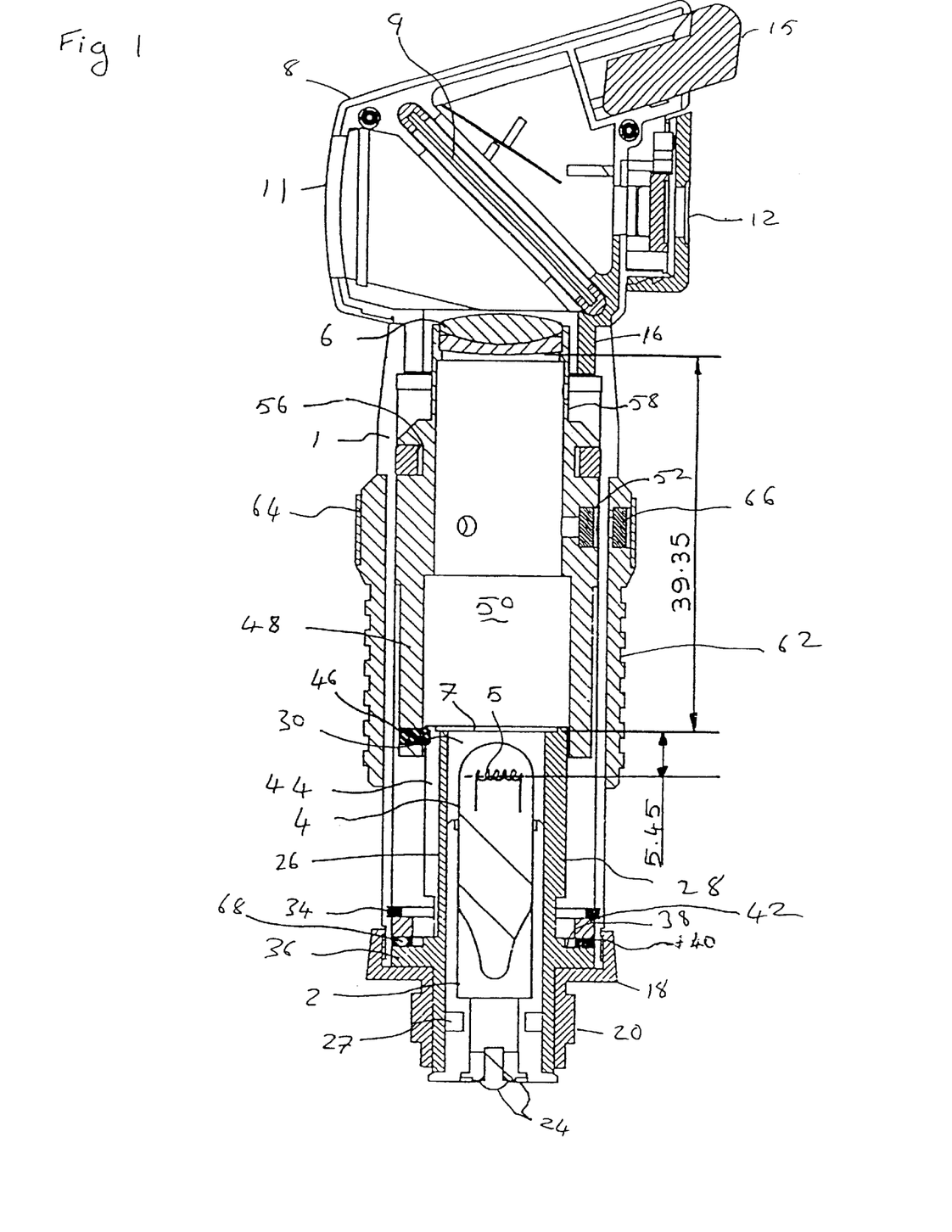
FIG. 1 is a sectional side view of a retinoscope in accordance with the invention, the retinoscope having focusing means comprising a pair of lenses which, in FIG. 1, are shown in their furthest position from the light source for the retinoscope.
Figure 2:
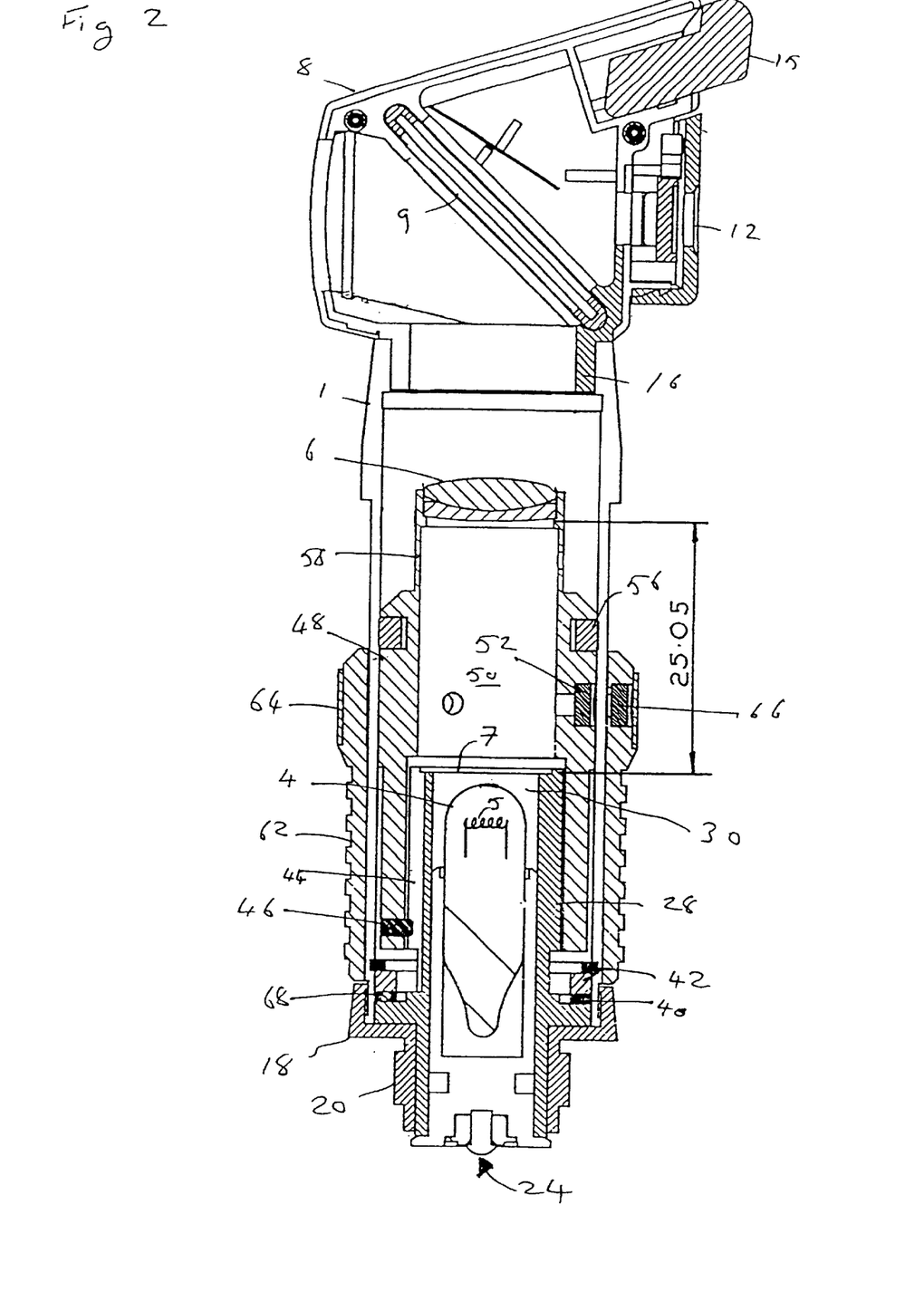
FIG. 2 is a corresponding view of the retinoscope with the lenses at their closest position to the light source.

The retinoscope shown in the drawings has a housing comprising a cylindrical body 1 of a non ferromagnetic material (for example aluminium) which contains a lamp body 2 which carries a halogen light bulb 4. The lamp 4 as shown in FIGS. 1 and 2 causes the retinoscope to function as a spot retinoscope, and to that end has a helical filament 5 for illuminating an annular stop ring 7. In use, light emitted by the filament passes through focusing means comprising a vergence lens system 6 situated towards the top of the body 1 and into a head 8.

The head 8 is identical to the head used in the KEELER VISTA STREAK retinoscope, and includes an angled half-silvered or apertured mirror 9 which reflects light travelling up from the lens system 6 through 90° to exit the head 8 through an aperture 11 in the front 10 thereof and into the eye under examination (not shown). When functioning as a spot retinoscope, the device forms an image of the illuminated portion of the area bounded by the stop 7 on the eye under examination, and thus projects a spot of light.

The projected image is viewed by the user of the retinoscope through the mirror 9 and a rear aperture 12.

The housing also accommodates a plate which is moved by means of a button and which includes two apertures, of different diameters, either of which can be selectively positioned in the viewing path from the mirror to the user to cause a selected degree of partial occlusion of the aperture 12 to occur. The head is also equipped with an orbital/brow rest 15.

The features of the head 8 are not described in detail because they are already known from the KEELER VISTA STREAK retinoscope.

The head 8 has a collar 16 which is externally screw-threaded and is screwed onto the top of the body 1. The bottom of the body 1 is externally screw-threaded so as to receive and retain a base cap 18. The base cap 18, in turn, includes a screw-threaded connector 20 for attachment to a handle (not shown), such as is used on the KEELER VISTA STREAK retinoscope, which handle also contains batteries for operating the lamp 2. The base cap 18 includes a through bore through which the lamp body 2 extends.

The bottom of the body 2, referenced 24, includes terminals for connecting the lamp 2 and hence the bulb 4 to a battery power supply in the handle. The lamp body 2 is securely held within an annular lamp holder 26 by means of an "o"-ring 27. The lamp holder 26 has an upstanding cylindrical wall 28 which defines a central passage 30 which accommodates the upper portion of the lamp. At the bottom of the wall 28, the holder 26 has a radial flange 36. The flange 36 is situated below a circlip 34 which sits in an annular groove on the inside of the body 1.

When the handle is attached, the terminals in the handle make contact with the bottom 24 of the body 2 and exert an upward biasing force on the lamp 2, and hence on the holder 26. The flange 36 defines an annular upward shoulder 38 which is therefore urged against three balls (e.g. 68), held in a race 40 which is in turn urged up against a thrust washer 42 located against the underside of the circlip 34. The lamp holder 26 also extends through the connector 20. The dimensions of the lamp holder are such that it, and hence the lamp body 2 (and bulb 4), is rotatable within the body 1 about the elongate axis of the latter.

The stop ring 7 is attached to the top of the wall 28.

The wall 28 of the lamp holder 26 includes an axial slot 44 into which a peg 46 extends (FIG. 2). The peg 46 projects radially inwards from an inner sleeve 48, which is rotatably retained in the body 1. The peg 46 provides a rotational key between the lamp holder 26 and the inner sleeve 48.

The inner sleeve 48 is also axially slidable along the inside of the body 1 and defines a central passage 50 for light from the bulb 4. The inner sleeve 48 also includes six equi-angularly spaced recesses in its outer surface. One such recess is shown at 52. Each of these recesses accommodates a respective rare earth magnet, such as the magnet 54. Each magnet is arranged with one pole facing radially outwards and the other radially inwards. Furthermore, the polar orientations of the magnets alternate so that each magnet which is orientated with its north pole facing outwards is positioned between two immediately neighbouring magnets, the south poles of which face outwards, and vice versa.

The outer surface of the sleeve 48 is also provided with an annular groove which accommodates a split washer 56 which, in use, presents a greater resistance to sliding of the sleeve 48 along the body 1 than it does to rotation of the sleeve 48 about the axis of the body 1. The top of the inner sleeve 48 includes a reduced diameter cylindrical portion 58 which extends upwards from an annular step 60, and to which the lens system 6 is adhered.

Figure 7:
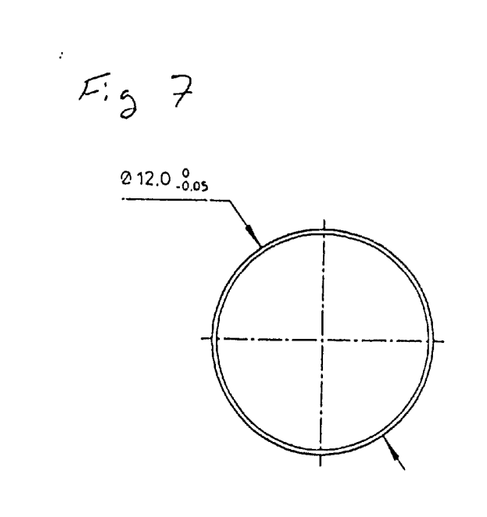
FIGS. 7 and 8 are views, respectively corresponding to FIGS. 5 and 6, of the second element of the doublet of lens for the focusing means.
Figure 8:
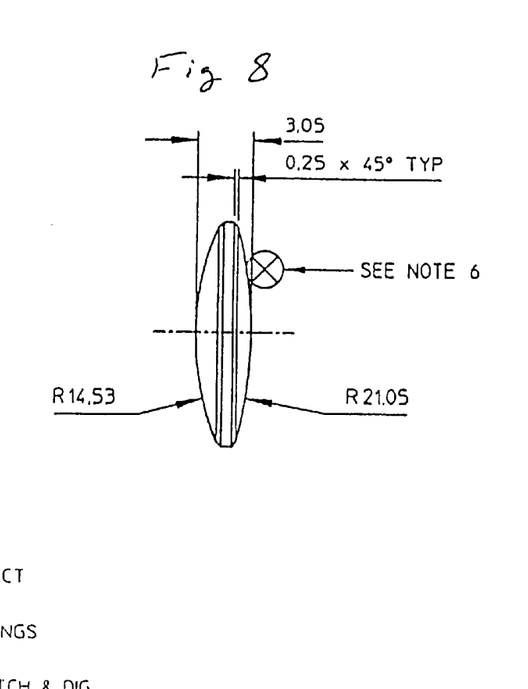

The lens system 6 is only diagrammatically represented in FIGS. 1 to 4, and is shown in more detail in FIGS. 5, 6, 7 and 8. The system comprises a doublet, the first element of which is a convex meniscus lens 72 of SF2 glass, and having a single layer Magnesium Fluoride anti-reflective coating (400–700 nm) centred on 550 nm, on its external surface. The various dimensions of the lenses (including radii of curvature in millimetres) are indicated on the drawings. The second element is a bi-convex lens as shown in FIGS. 7 and 8. This lens is formed from glass type BK7.

The inner sleeve 48, and hence the lamp 22 and the lens system 6 can be rotated within the body 1 and the lens system 6 can be moved axially along the body, by means of a control member comprising an external sleeve 62 which is slidably and rotatably mounted on the exterior of the housing 1.

The sleeve 62 includes a trim ring 64 below which six rare earth magnets such as the magnet 66 are accommodated by the sleeve 62. Each of the magnets in the ring 64 cooperates with a respective corresponding magnet on the sleeve 48, in angular registry therewith. To that end the magnets are arranged in an annular formation, with the pole of each magnet which faces radially inwards being opposite to the pole of the corresponding magnet on the sleeve 48. Thus, a magnet in the sleeve 62 which is in angular registry with, and therefore cooperates with, a magnet (on the sleeve 48) orientated with its south pole facing outwards, will be arranged with its north pole facing radially inwards.

The magnets in the sleeve 62 and those mounted on the sleeve 48 provide a coupling between the sleeve 62 and sleeve 48 which acts through the wall of the body 1, and therefore avoid requirements for any apertures in the body 1 to provide a direct mechanical connection between the two components.

Also, since the sleeve 62 encircles the body 1, access to the sleeve 62 is not restricted by any part of the body 1.

In use, the orientation of the bulb 4 is adjusted by rotating the sleeve 62 about the exterior of the body 1. This causes the magnets in the sleeve 62 to act on the magnets in the sleeve 48 so as to cause a corresponding rotation of the sleeve 48, and hence the lamp body 2 and lens system 6. While this happens, the split washer 56 prevents the sleeve 48 from sliding along the inside of the body 1 (and thus from altering the focus of the image on the eye under examination). If the focusing provided by the vergence lens 6 is to be adjusted, the sleeve 62 is slid axially along the housing 1, causing a similar axial movement of the inner sleeve 48, and hence the lens 6.

If, during rotational movement, the inner sleeve 48 and outer sleeve 62 begin to move out of registry with each other, then the attractive forces between each magnet in the ring 64 and its corresponding magnet on the sleeve 48 are supplemented by repulsive forces between each magnet in the ring 64 and one of the neighbours of the corresponding magnets on the sleeve 48. When the retinoscope is arranged, as shown in FIGS. 1 and 2, to function as a spot retinoscope, the rotation of the sleeve 62, and hence the lamp 4, does not affect the appearance of the patch of light projected by the retinoscope into the eye under examination. This is because the patch is substantially circular, with the shadow cast by the stop 7 defining the boundary of the patch, and is therefore symmetrical about the axis about which the lamp sits, and hence the beam of projected light, rotates. However, sliding of the sleeve 62 along the body 1 will adjust the distance between the lens system 6 and the bulb 4 and stop 7. This movement enables adjustment of the convergence or divergence of the beam of light emitted by the retinoscope.

FIG. 2 shows the lens system when in its closest position to the bulb 4 and stop 7, in which the distance between the lens system 6 and the stop 7 is 25.05 mm. When the lens system 6 is in this position, the beam emitted by the retinoscope has its greatest divergence, and therefore projects a relatively large spot into the eye under examination. The size of the projected spot can be reduced by sliding the sleeve 62 up the body 1, so as to increase the distance between the lens system 6 and the stop 7, and thereby reduce the degree of divergence of the emitted beam. Once the beams of varying divergence have been used to find what is believed to be the "neutral point" (in conjunction with one or more correcting lenses interposed between the retinoscope and the eye under examination), the user moves the sleeve 62 to its uppermost position as shown in FIG. 1, in which the lens system 6 is then 39.35 mm from the stop 7.

This causes the beam emitted by the retinoscope to converge to a point around 300 mm from the retinoscope.

This position is the cross-check position in which movement of the retinoscope will cause a detectable amount of movement in the opposite direction of the reflex from the eye under examination if the neutral point has not been reached. As has been explained above, the direction of that movement relative to the movement of the retinoscope, will be opposite to the direction of the small amount of movement (which was not detected by the user) of the reflex before the cross-check procedure was carried out. As can be seen from FIG. 1, the filament 5 of the bulb 4 is 5.45 mm further away from the lens system 6 than the stop 7. As a result, the central aperture of the stop 7 appears uniformly illuminated in the projected image.

Figure 3:
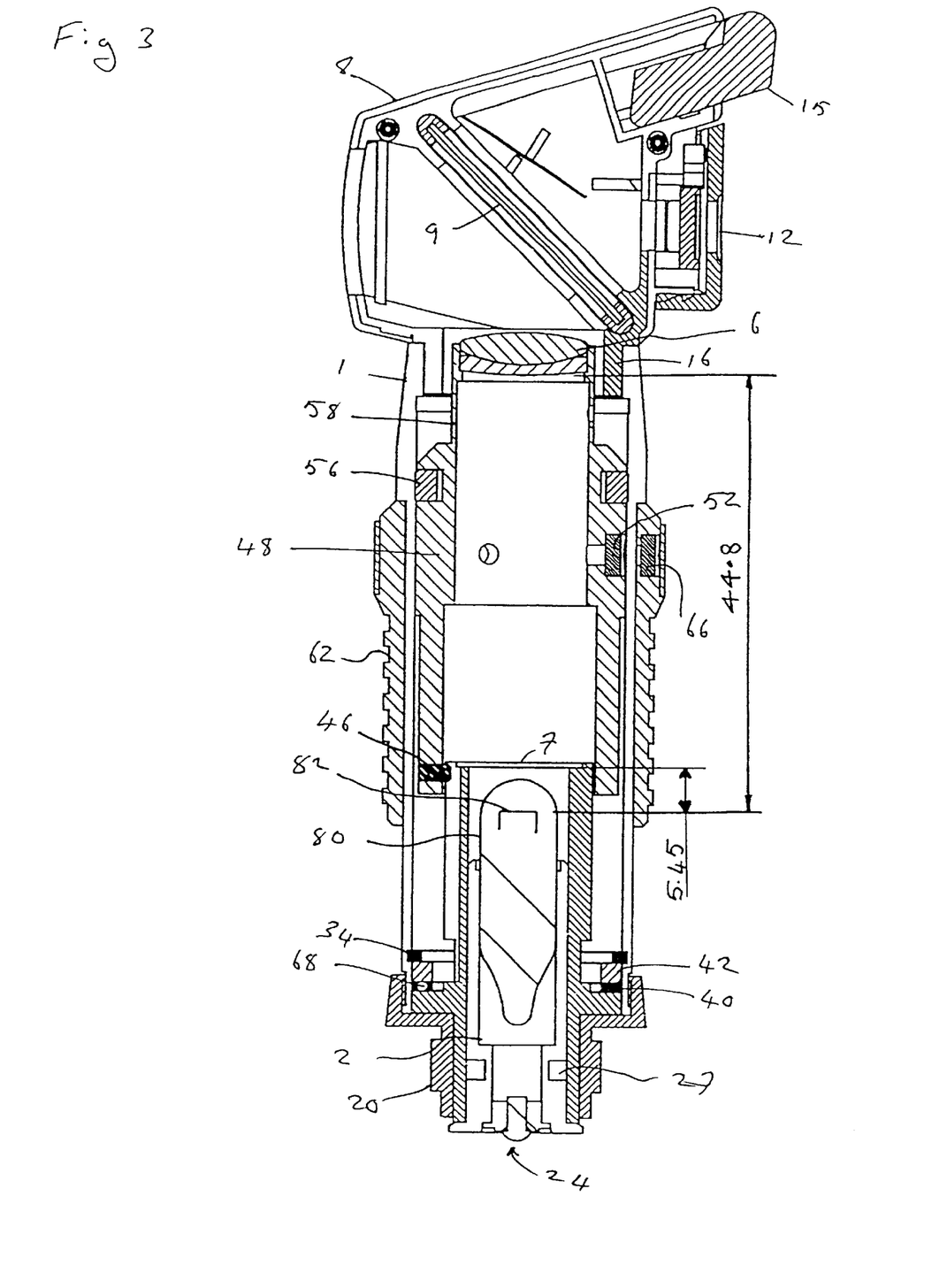
FIG. 3 is a sectional side view of the retinoscope when arranged to function as a streak retinoscope, the Figure showing the lenses at their furthest position from the light source.
Figure 4:
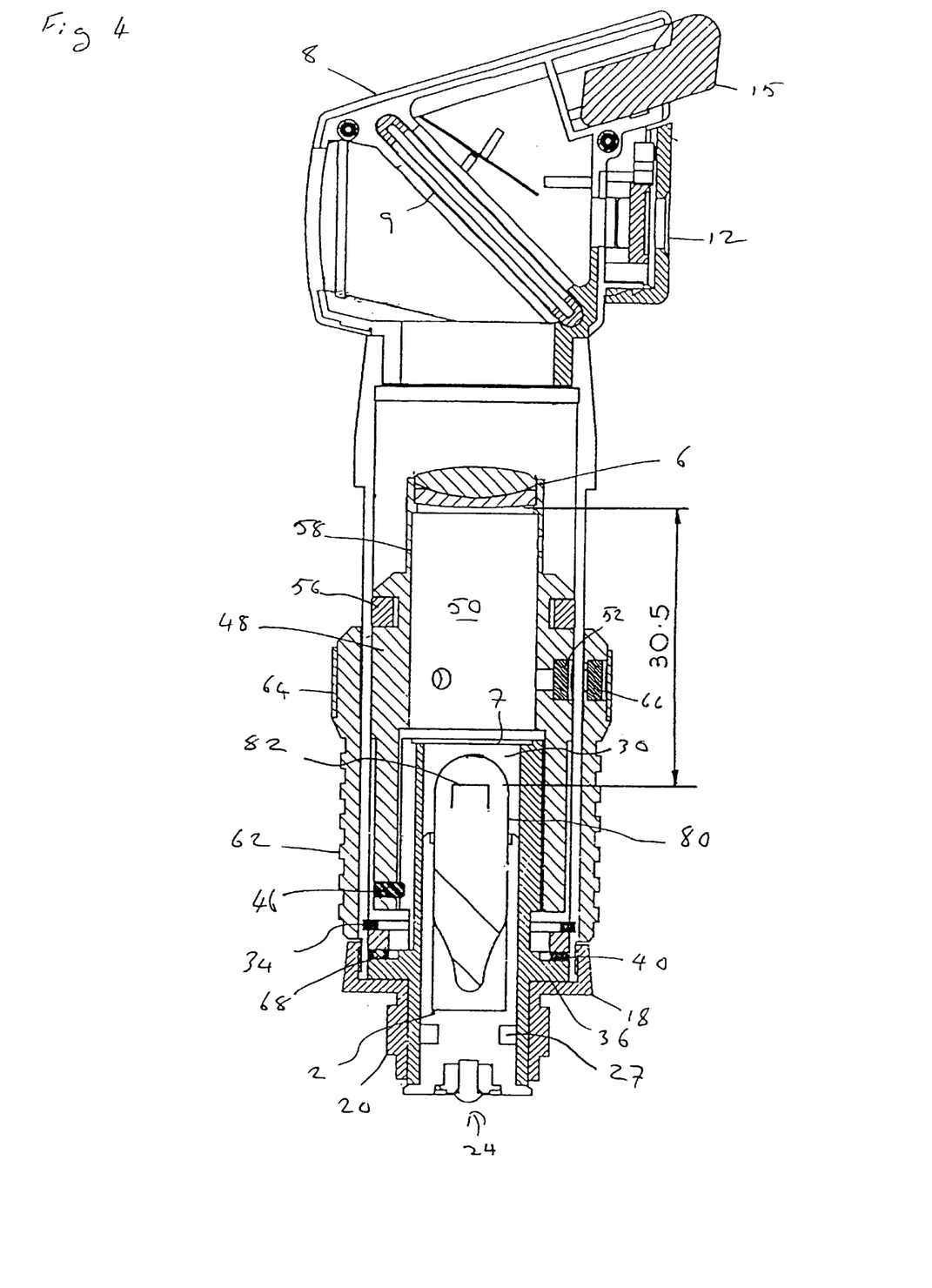
FIG. 4 is a view which corresponds to FIG. 3, and shows the lenses at their closest position to the light source.
Figure 5:
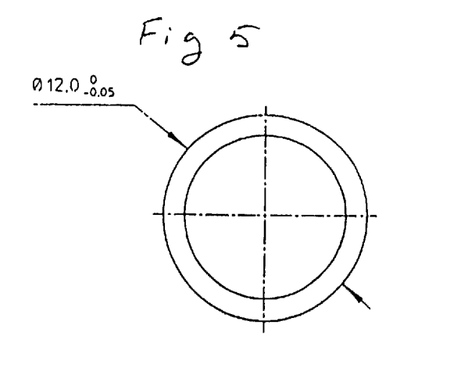
FIG. 5 is a front view of the element of a doublet lens for use as the focusing means of the retinoscope.
Figure 6:
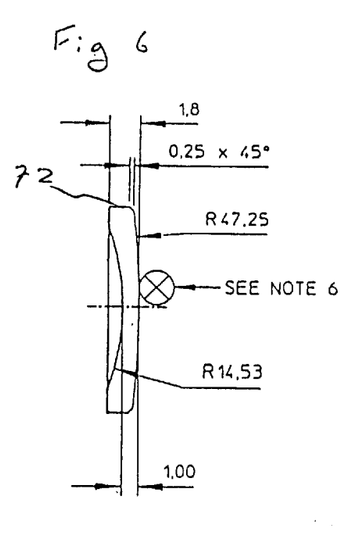
FIG. 6 shows the same lens in a section from one side.

The bulb 4 is interchangeable with a "streak" bulb 80 of the type shown in FIGS. 3 and 4. This bulb differs from the bulb 4 only in that it has a single linear filament 82 instead of the helical filament 5. As can be seen from FIG. 3, this filament is also set back from the stop 7 by 5.45 mm. However, the range of allowable movement of the lens system 6 (14.3 mm) along the housing 1 is such that the lens system 6 can project a focused image of the filament 82 onto the eye under examination, to enable to retinoscope to be used as a streak retinoscope. In this case, the rotation of the sleeve 62, and hence the bulb 82, will have a visible effect since the streak of light projected onto the eye under examination will be seen to rotate in the same sense as the sleeve 62. The retinoscope can still provide a cross-check function since the lens system 6 can be moved to a position of approximately 39 mm from the filament 7.

What is claimed is:

1. A spot retinoscope for use in assessing the refractive error of an eye, the retinoscope having viewing means for viewing the eye under examination, receiving means for receiving a source of light, projection means for directing a beam of light from a source in the receiving means into an eye under examination thereby to project a spot of light into said eye, and focusing means for altering the divergence and convergence of said beam, the focusing means being movable from a normal position in which the beam is divergent, or converges to a point, in use, behind the eye under examination, to a cross-checking position, in which the beam is convergent on a point which, in use, is sufficiently far in front of the eye under examination to enable the user to detect movement of the patch of light projected onto the retina under examination where any refractive error in said eye has not been corrected by a lens placed between the eye and the retinoscope.

2. A spot retinoscope according to claim 1, in which the focusing means is so arranged that when the focusing means is in its cross-check position, it causes the beam of light emitted by the retinoscope to converge on a point not more than approximately 300 mm from the retinoscope.

3. A retinoscope according to claim 1, in which the retinoscope includes a light source for emitting the light for said beam, said source being held by said receiving means.

4. A retinoscope according to claim 3, in which the light source is interchangeable with a further light source, the further light source being arranged to emit light over an elongated substantially linear area to cause the retinoscope to project a streak of light into the eye under examination, the retinoscope including rotation means for rotating the streak to enable to retinoscope to be used as a streak retinoscope.

5. A retinoscope according to claim 4, in which the retinoscope includes said further source, and the further light source has a linear light-emitting element, the projected image of which constitutes said streak.

6. A retinoscope according to claim 5, in which the retinoscope includes a stop situated in the path of light from the light source and arranged to cast a shadow that bounds the beam of light projected from the retinoscope so as to cause a spot of light to be projected into the eye under examination, the light source being such as to provide substantially uniform illumination of the spot.

7. A retinoscope according to claim 6, in which the stop is annular.

8. A retinoscope according to claim 6, in which the light source comprises a bulb having a helical filament.

9. A retinoscope according to claim 6, in which the range of movement of the focusing means is such as to enable an image of either the inner periphery of the stop or, where the further light source is used, the linear element to be projected into the eye under examination.

10. A retinoscope according to claim 9, in which the focusing means comprises lens means which is slidably mounted in the retinoscope and is movable towards or away from the stop and light source over a distance of at least 14 mm.

11. A retinoscope according to claim 9, in which the focusing means is in its cross-check position when the lens means is furthest from the stop and light source.

12. A retinoscope according to claim 9, in which the rotation means and focusing means are connected to an external control member for operating the rotation means and adjusting the position of the focusing means, by a magnetic linkage.

13. A retinoscope according to claim 12, in which the control member comprises a sleeve which is slidably and rotatably mounted on the exterior of the retinoscope.

* * * * *